US006365156B1

(12) United States Patent
Lee

(10) Patent No.: US 6,365,156 B1
(45) Date of Patent: Apr. 2, 2002

(54) METHOD FOR IMPROVING THE HALF-LIFE OF SOLUBLE VIRAL-SPECIFIC LIGANDS ON MUCOSAL MEMBRANES

(75) Inventor: Peter P. Lee, Palo Alto, CA (US)

(73) Assignee: Osel, Inc., Santa Clara, CA (US)

( * ) Notice: Subject to any disclaimer, the term of this patent is extended or adjusted under 35 U.S.C. 154(b) by 0 days.

(21) Appl. No.: 09/549,261

(22) Filed: Apr. 14, 2000

Related U.S. Application Data

(60) Provisional application No. 60/129,722, filed on Apr. 16, 1999.

(51) Int. Cl.$^7$ .................. A61K 39/40; A61K 39/42; A61K 39/385
(52) U.S. Cl. .................. 424/147.1; 424/163.1; 424/164.1; 424/159.1; 424/196.1
(58) Field of Search .................. 424/434, 163.1, 424/165.1, 194.1, 196.11, 197.11, 199.1, 200.1, 201.1, 93.3, 400, 159.1, 164.1; 514/1

(56) References Cited

U.S. PATENT DOCUMENTS

| | | | |
|---|---|---|---|
| 5,348,867 A | | 9/1994 | Georgiou et al. |
| 5,531,988 A | | 7/1996 | Paul |
| 5,733,540 A | * | 3/1998 | Lee .................. 424/93.1 |
| 6,074,636 A | | 6/2000 | Nichols |

FOREIGN PATENT DOCUMENTS

| WO | WO 93/18163 | 9/1993 |
|---|---|---|

OTHER PUBLICATIONS

Eko et al. Mar. 1999. New strategies for combination vaccines based on the extended recombinant bacterial ghost system. Vaccine. vol. 17, pp. 1643–1649.*

Baba et al. 1996. Target cell specificity of a bacteriocin molecule: a C–terminal signal directs lysostaphin to the cell wall of Staphylococcus aureus. The EMBO Journal. vol. 15. No. 18, pp. 4789–4797.*

Braun et al. 1998. The InlB protein of Listeria monocytogenes is sufficient to promote entry into mammalian cells. Molecular Microbiology. vol. 27. No. 5, pp. 1077–1087.*

Marshall, E., "Gene Therapy's Growing Pains, " *Science,* 269:1050–1055 (Aug. 25, 1995).

Lidbeck, A., et al., "Lactobacilli in Relation to Human Ecology and Antimicrobial Therapy," 1991 Bioscience Ediprint, Inc., Int. J. Tiss. Reac. XIII(2):115–122 (1991).

Bouhnik, Y., et al., "Fecal Recovery in Humans of Viable Bifidobacterium sp Ingested in Fermented Milk," 1992 by the American Gastroenterological Association, *Gastroenterology,* 102:875–878 (1992).

Pochart, P., et al., "Survival of bifidobacteria ingested via fermented milk during their passage through the human small intestine: an in vivo study using intestinal perfusion$^{1-4}$," 1992 American Society for Clinical Nutrition, *Am J Clin Nutr* 55:78–80 (1992).

Laulund, S., "Commercial Aspects of Formulation, Production and Marketing of Probiotic Products," Human Health: The Contribution of Microorganisms Formulation, Production and Marketing of Probiotic Products, Chapter 10, 159–173 (1994).

* cited by examiner

*Primary Examiner*—James Housel
*Assistant Examiner*—Shanon A. Foley
(74) *Attorney, Agent, or Firm*—Townsend and Townsend and Crew LLP

(57) ABSTRACT

This invention relates to methods of increasing the half-life of a viral-specific ligand on a mucosal membrane by modifying the viral-specific ligand to bind the bacteria colonized on the mucosal membrane. The invention also provides a chimeric molecule comprising a viral-specific ligand and a bacterial-specific ligand.

19 Claims, 1 Drawing Sheet

METHOD FOR IMPROVING THE HALF-LIFE OF SOLUBLE VIRAL-SPECIFIC LIGANDS ON MUCOSAL MEMBRANES

CROSS-REFERENCES TO RELATED APPLICATIONS

This application claims the priority of United States Provisional Application No. 60/129,722, filed on Apr. 16, 1999, the disclosure of which is hereby incorporated by reference.

STATEMENT AS TO RIGHTS TO INVENTIONS MADE UNDER FEDERALLY SPONSORED RESEARCH AND DEVELOPMENT

Not applicable.

BACKGROUND OF THE INVENTION

The use of soluble viral receptors to prevent viral infection is being actively pursued. Amongst these efforts, intranasal administration of soluble ICAM-1 is being tested to prevent rhinovirus (cold) infection (Boehringer Ingelheim and Bayer). Soluble viral receptors are designed to work by engaging all host binding sites of a virus, thereby leaving none for the virus to attach to its target cell. However, a single viral particle has numerous binding sites for the host cell on its surface, e.g. rhinovirus has 60. Soluble viral receptors must simultaneously coat all binding sites on the virus to render it non-infectious. This requires an extremely high ratio of soluble viral receptors to viral particles (e.g. >60:1 for rhinovirus). Furthermore, since binding is a reversible process, it is unlikely that all binding sites on a virus could be coated simultaneously. Theoretically, even one free binding site on a virus would still allow it to be infectious to the host.

Clinical trials with soluble viral receptors to prevent viral infection have been met with limited success. Soluble ICAM-1 receptors were found to be only minimally effective in preventing cold infections, and only if they were already present on the nasal mucosa at the time of encounter with rhinovirus. Since an infected host is unaware of any symptoms until 2 to 3 days after an infection occurs, the only way to ensure that soluble viral receptors are present on the nasal mucosa at the time of infection is to apply them regularly throughout a period of presumed risk.

In particular, there is a problem of the short half-life of the soluble viral receptors on the mucosal surface. Since soluble viral receptors are freely mobile, they can be easily washed out by the normal mucociliary clearance mechanisms. This translates into a need for frequent reapplications. Subjects in the ICAM study had to apply the soluble viral receptors six times per day. This will likely translate into high cost and poor compliance, making soluble ICAM-1 receptor therapy an impractical approach for preventing cold infections.

The purpose of this invention is to improve the half-life of soluble viral-specific ligands on mucosal membranes, thereby reducing the cost and application frequency associated with the use of soluble viral-specific ligands to prevent viral infection.

SUMMARY OF THE INVENTION

Figure 1:
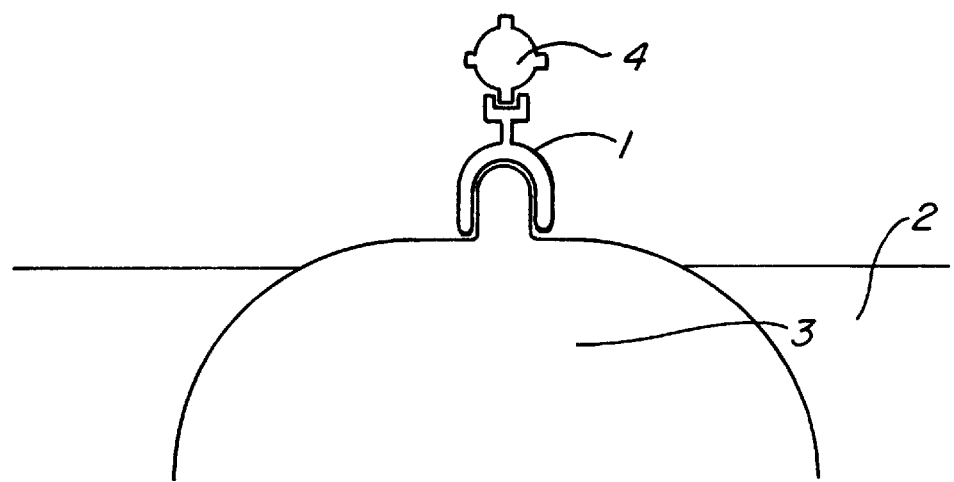
FIG. 1 is a cartoon illustration of a chimeric molecule binding a viral particle to the surface of a bacterial cell colonizing a mucosal membrane. This cartoon illustrates a binding a viral particle (4) to a bacterium (3) inhabiting the mucosal membrane (2) of an animal with a (1) soluble, viral-specific ligand modified with a bacteria-binding domain which is specific for bacteria colonizing the mucosa. Alternatively, (1) can be a chimeric molecule having a viral-specific ligand and a bacterial-specific ligand.
Figure 2:
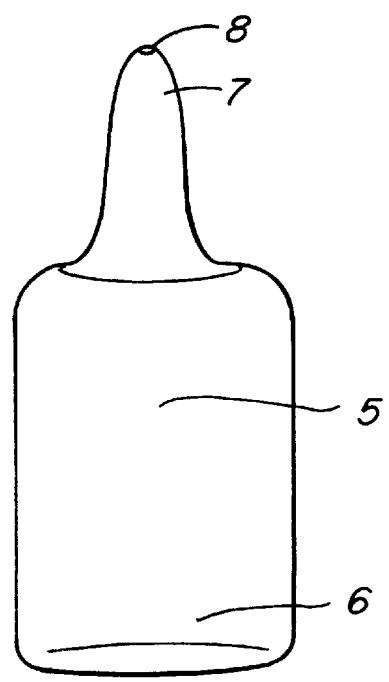
FIG. 2 is an elevation of a container suitable for delivering the chimeric molecules as an aerosol onto nasal passages.

This invention provides for a method of increasing the half life of a viral-specific ligand on a mucosal membrane of an animal wherein said membrane is colonized with bacteria, said method comprising: contacting the mucosal membrane with a viral-specific ligand modified to bind to the surface of bacteria colonizing the membrane. A variety of different bacteria can be targeted. For example, the viral-specific ligand can be modified to bind to Streptococcus, Lactobacillus, Streptococcus, Staphylococcus, Lactococcus, Bacteriodes, Bacillus, and Neisseria. The viral-specific ligand can be modified using a bacterial-specific ligand that is an antibody, a polypeptide, a protein, a peptide, a lipid, or a carbohydrate, or combination thereof, specific for a component of the extracellular material of the bacteria. Alternatively one can use antibody fragments, single chain antibodies, F(ab)s, F(ab)2s or bacterial specific non-antibody binding elements. The bacterial-specific ligand can also be selected from the group consisting of: a C-terminal choline binding domain of LytA, a C-terminal binding domain of PspA, a C-terminal domain of lysostaphin ($SPA_{CWT}$), a C-terminal domain of InIB, an anti-S-layer protein antibody, and an anti-peptidoglycan antibody.

The viral-specific ligand and the bacterial-specific ligand can be joined by a variety of means. These include bifunctional linkers both hetero and homobifunctional linkers and peptide linkers.

The invention provides for viral-specific ligands, where the viral-specific ligand is comprised of a peptide, a polypeptide, a protein, a carbohydrate, or a combination thereof. The viral-specific ligands of the present invention can also be an antibody or an antibody selected from the group consisting of: a single-chain antibody, a F(ab), and a F(ab)2. The viral-specific ligand of the present invention can be modified by covalently binding a bacterial-specific ligand to said viral-specific ligand.

The viral-specific ligand of the present invention can be comprised of CD4, DC-SIGN, ICAM-1, HveC, poliovirus receptor, vitronectin receptor, CD21 and HveA receptor sequences. The viral-specific ligand can also be a carbohydrate such as sialic acid or heparin sulfate.

The invention further provides for a chimeric molecule that is a bifunctional molecule comprising a viral-specific ligand and a bacterial-specific ligand. The bacterial-specific ligand binds to a bacterium that is a natural inhabitant of a mucosal membrane.

In addition to the methods described above, this invention includes the chimeric molecules themselves. The chimeric molecule can be as described above and it can be manufactured as a dry product, e.g. lyophilized or as a solution in combination with a sterile aqueous solution. The solution is a physiologically compatible solution.

This invention further provides for a method of manufacturing the chimeric molecules described above said method comprising the step of joining a viral-specific ligand with a bacterial-specific ligand wherein the binding domain binds to a bacteria that is an inhabitant of a mucosal membrane and the viral-specific ligand binds to infectious viral particles.

The manufacturing method can also include the step of solubilizing the chimeric molecule as a unit dose in a sterile, pharmaceutically acceptable solution.

This invention further provides for a method of binding viral particles to bacteria inhabiting the mucosal membrane of an animal comprising the step of contacting the bacteria with a soluble, viral-specific ligand modified to have a bacterial-specific ligand which is specific for bacteria colonizing the mucosa and permitting viral particles specifically recognized by the soluble, viral-specific ligand to be immobilized on to the bacteria.

This invention further provides for a system for delivering a unit dose of chimeric molecule to nasal mucosa in a physiologically compatible solution comprising: (i) a chimeric molecule in a sterile, pharmaceutically acceptable solution the chimeric molecule comprising a viral-specific ligand and a bacterial-specific ligand wherein the bacterial-specific ligand binds to a bacteria that is a natural inhabitant of a healthy mucosal membrane and (ii) a container having first and second ends, wherein the first end is a base for containing the solution and the second end is a tapered tip having an opening for delivering a metered and aerosol spray of the solution into a nasal passage. The system may preferably include a container where the first end is flexible and allows for the transfer of external pressure from the container to the solution allowing the fluid to be forcibly emitted from the second end of the container as an aerosol spray.

This invention further provides for a pharmaceutical composition comprising a therapeutically effective amount of a chimeric molecule or a viral-specific ligand modified by binding a bacterial-specific ligand. The pharmaceutical can be formulated as a solution, a powder, a cream, a gel, an ointment, a douche, a suspension, a tablet, a pill, a capsule, a nasal spray, a nasal drop, a suppository and an aerosol. Alternatively, the pharmaceutical composition can be formulated as a pessary, a tampon, a gel, a paste, a foam, and a spray

DESCRIPTION OF THE SPECIFIC EMBODIMENTS

A. INTRODUCTION

Mucosal membranes are colonized with large numbers of resident commensal bacteria. If soluble viral-specific ligands are immobilized onto the surface of these mucosal bacteria, viral-specific ligand half-life will be significantly improved. First, soluble viral-specific ligands immobilized onto mucosal bacteria would be much less prone to be flushed out by the mucociliary clearance mechanisms on the mucosa. This will reduce the dosing of, for instance, soluble ICAM (e.g. for immobilizing rhinovirus) from six-times to once or twice daily, vastly improving the likelihood of patient compliance and reducing cost. In addition, when viral particles bind to soluble viral-specific ligands that are immobilized onto mucosal bacteria, they too will be immobilized onto the bacteria (see FIG. 1).

The viral-specific ligands can be immobilized to bacteria with a bacterial-specific ligand. The bacterial-specific ligand can be used to modify the viral-specific ligand or associated with the viral-specific ligand to form a chimeric molecule. The viral-specific ligand serves to bind the viral particle and the bacterial-specific ligand immobilizes the viral particle/viral-specific ligand complex to the surface of the bacteria.

Since bacteria are generally considerably larger than viral particles, the viral particles will be prevented from moving on to infect host cells. In this way a single soluble viral-specific ligand interaction immobilizes and renders a viral particle non-infectious, rather than requiring as many soluble viral-specific ligands as there are binding sites on the virus particles, e.g. 60 for rhinovirus, if the soluble viral-specific ligands and virus were freely mobile.

Another potential mechanism of neutralization is through viral disruption. After binding to soluble viral-specific ligands immobilized onto a rigid bacterial cell wall, disruption of some viral particles will occur due to geometric distortion to the viral particle. Finally, immobilization of soluble viral-specific ligands onto mucosal bacteria will significantly decrease the cost associated with this approach both by decreasing the number of times per day and amount of drug per dose needed.

B. DEFINITIONS

"Antibody" refers to a protein functionally defined as a binding protein and structurally defined as comprising an amino acid sequence that is recognized by one of skill as being derived from the framework region of an immunoglobulin encoding gene of an animal producing antibodies. An antibody can consist of one or more polypeptides substantially encoded by immunoglobulin genes or fragments of immunoglobulin genes. The recognized immunoglobulin genes include the kappa, lambda, alpha, gamma, delta, epsilon and mu constant region genes, as well as myriad immunoglobulin variable region genes. Light chains are classified as either kappa or lambda. Heavy chains are classified as gamma, mu, alpha, delta, or epsilon, which in turn define the immunoglobulin classes, IgG, IgM, IgA, IgD and IgE, respectively.

A typical immunoglobulin (antibody) structural unit is known to comprise a tetramer. Each tetramer is composed of two identical pairs of polypeptide chains, each pair having one "light" (about 25 kD) and one "heavy" chain (about 50–70 kD). The N-terminus of each chain defines a variable region of about 100 to 110 or more amino acids primarily responsible for antigen recognition. The terms variable light chain (VL) and variable heavy chain (VH) refer to these light and heavy chains respectively.

Antibodies exist as intact immunoglobulins or as a number of well-characterized fragments produced by digestion with various peptidases. Thus, for example, pepsin digests an antibody below the disulfide linkages in the hinge region to produce F(ab)'2, a dimer of Fab which itself is a light chain joined to VH-CH1 by a disulfide bond. The F(ab)'2 may be reduced under mild conditions to break the disulfide linkage in the hinge region thereby converting the (Fab')2 dimer into a Fab' monomer. The Fab' monomer is essentially a Fab with part of the hinge region (see, Fundamental Immunology, W. E. Paul, ed., Raven Press, N.Y. (1993), for a more detailed description of other antibody fragments). While various antibody fragments are defined in terms of the digestion of an intact antibody, one of skill will appreciate that such Fab' fragments may be synthesized de novo either chemically or by utilizing recombinant DNA methodology. Thus, the term antibody, as used herein also includes antibody fragments either produced by the modification of whole antibodies or synthesized de novo using recombinant DNA methodologies. Preferred antibodies include single chain antibodies (antibodies that exist as a single polypeptide chain), more preferably single chain Fv antibodies (sFv or scFv) in which a variable heavy and a variable light chain are joined together (directly or through a peptide linker) to form a continuous polypeptide. The single chain Fv antibody is a covalently linked VH-VL heterodimer which may be expressed from a nucleic acid including VH- and VL-encoding sequences either joined directly or joined by a peptide-encoding linker. Huston, et al. (1988) Proc. Nat.

Acad. Sci. USA, 85: 5879–5883. While the VH and VL are connected to each as a single polypeptide chain, the VH and VL domains associate non-covalently. The first functional antibody molecules to be expressed on the surface of filamentous phage were single-chain Fv's (scFv), however, alternative expression strategies have also been successful. For example Fab molecules can be displayed on phage if one of the chains (heavy or light) is fused to g3 capsid protein and the complementary chain exported to the periplasm as a soluble molecule. The two chains can be encoded on the same or on different replicons; the important point is that the two antibody chains in each Fab molecule assemble post-translationally and the dimer is incorporated into the phage particle via linkage of one of the chains to g3p (see, e.g., U.S. Pat. No: 5,733,743). The scFv antibodies and a number of other structures converting the naturally aggregated, but chemically separated light and heavy polypeptide chains from an antibody V region into a molecule that folds into a three dimensional structure substantially similar to the structure of an antigen-binding site are known to those of skill in the art (see e.g., U.S. Pat. Nos. 5,091,513, 5,132,405, and 4,956,778). Particularly preferred antibodies include all those that have been displayed on phage (e.g., scFv, Fv, Fab and disulfide linked Fv (Reiter et al. (1995) Protein Eng. 8: 1323–1331). Antibodies can also include diantibodies and miniantibodies.

"Bifunctional linking reagent" or "bifunctional linkers" refers to a molecule with one functional group reacting with a chemical moiety on a first molecule and a second functional group reacting with a chemical moiety on a second molecule. Bifunctional linking reagents can be used to link two different molecules via such functional groups.

"Chimeric" refers to the combination of two molecules from different sources. A "chimeric molecule" is a bifunctional molecule. An example of a chimeric molecule is a viral-specific ligand that is modified to include a non-native domain, i.e. a bacterial-specific ligand. The molecules may be physically associated through a variety of means, including but not limited to, ionic bonds, covalent bonds or hydrophobic interactions.

A "domain" is a region of a molecule that has a defined functional attribute. Domains can refer to proteins, carbohydrates or lipids. The domains can be made in a variety of ways. Also the domains can be derived from or homologous to naturally occurring molecules. Alternatively, the domains can be isolated from a library of molecules made up of polymers with sequences not occurring in nature. Examples of "domains" include a "viral-specific ligand" and a "bacterial-specific ligand".

A "ligand" is a molecule which has the ability to bind to another molecule. A ligand can be any ion or molecule with binding properties. Examples of classes of ligands include, without limitation, ions, organic molecules, inorganic molecules, peptides, proteins, polypeptides, carbohydrates, lipids, and polymers.

A "viral-specific ligand" refers to a molecule which has the ability to bind to, without limitation, a viral particle, protein, carbohydrate, lipid, or surface molecule that is not produced by a host cell infected with virus. The binding is considered specific when more of the domains binds to the viral particle than to the background of mucosa. The viral-specific ligand can comprise a region(s) of a receptor which binds to a molecule on a virus. The viral-specific ligand can be comprised of extracellular regions of molecules expressed on the surface of cells which are responsible for the ability of the molecule to bind viral particles. For example, viral-specific ligands can be found in a molecule such as CD4, which is important for HIV binding to cells. Viral-specific ligands may also be isolated from combinatorial peptide libraries or from libraries encoding sequences from a patient(s) seropositive for a virus. Viral-specific ligands can be, without limitation, antibodies (e.g., single chain antibodies, antibodies, Fab, and other antibody fragments), peptides, and small organic molecules. Essentially, viral-specific ligands can be identified or isolated from any source as long as the viral-specific ligand possesses the ability to bind to a viral molecule or viral particle. Viral-specific ligands can be organic and inorganic molecules. Such molecules may be identified through screening of a library.

The term "bacterial-specific ligand" refers to a molecule that interacts with and binds to, without limitation, a protein, carbohydrate or lipid on the surface, including the membrane or cell wall, of a bacterium. The binding is considered specific when more of the ligands binds to the target bacteria than to the background of mucosa. Bacterial-specific ligands may also be isolated from combinatorial peptide libraries or from libraries comprised of nucleic acid sequences from bacteria, mammals, viruses, or plants. Bacterial-specific ligands can be antibodies (e.g., single chain antibodies, Fab, and other antibody fragments), peptides, and small organic molecules. Essentially, bacterial-specific ligands can be identified or isolated from any source as long as the bacterial-specific ligand possesses the ability to bind to a bacterial molecule or bacterium. Bacterial-specific ligands can be organic and inorganic molecules. Such molecules may be identified through screening of a library.

"Half life" refers to the period of time it takes for an animal or animal tissue to clear 50% of a particular substance from that animal or animal tissue.

The phrase "modified to bind" in the context of a viral-specific ligand means that the viral-specific ligand binds or attaches to a bacterium in a specific manner so that in an assay to test for binding, the modified viral-specific ligand binds at least two times greater an amount than an unmodified viral-specific ligand under controlled experimental conditions.

"Natural inhabitants of healthy mucosal membranes" refer to microorganisms, such as bacteria, that commonly reside on mucosal membranes of animals and are non-pathogenic to their host.

"Mucosal or mucous membrane" refers to a tissue layer found lining various tubular cavities of the body (as the gut, uterus, trachea, etc). It is composed of a layer of epithelium containing numerous unicellular mucous glands and an underlying layer of areolar and lymphoid tissue, separated by a basement membrane. This membrane is typically colonized by a variety of bacteria even when the host is healthy.

A "peptide linker" or a "peptide linkage" refers to a link between two molecules wherein that link is formed by a covalent bond between the amino group ($NH_3^+$) of one amino acid and the carboxyl group ($COO^-$) of another amino acid. One of skill in the art will recognize that such links need not occur along a polypeptide backbone. The links may also form, e.g., along the functional groups of a variety of amino acids such as, the $COO^-$ functional groups of aspartate and glutamate, as well as the $NH_3^+$ functional groups of, e.g., lysine or arginine. One of skill in the art will also recognize that a peptide linker is not limited to the peptide bond itself, but may also include additional amino acids or other chemical moieties to link the two molecules.

"Physiologically compatible solution" refers to a solution which is not detrimental or harmful to the health of a patient when placed in contact with the solution.

"Soluble viral-specific ligand" refers to a viral-specific ligand can exist free in solution and is not bound to a native cell or source of origin. When in an aqueous solution, they can be in suspension, partially or fully solvated by the solution.

A molecule is "soluble" if it can exist free in solution.

"Sterile" refers to a solution which has a low quantitative number of virus, living bacteria and fungi and which number meets FDA requirements for aseptic solutions suitable for contact with human tissue.

"Surface" as applied to bacteria refers to the extracellular matrix, the cell wall and the cell membrane of the bacteria.

"Unit dose" or "unit dosage" refers to a measured and quantified amount of an active ingredient in a pharmaceutical preparation.

"Viral-specific ligand" refers to a molecule, such as a polypeptide or a carbohydrate, which interacts with a virus. Some viral-specific ligands are expressed by cells and bind to a viral particle, thereby allowing the virus to enter a cell. "Viral-specific ligands" can be derived from screening of a peptide library or chemical library. Moreover, the "viral-specific ligand" does not have to be homologous to a host cell sequence. When a part of the chimeric molecules of this invention, the viral-specific ligands bind and hold viral particles preventing their ability to subsequently bind to their target host cells to begin the infection process.

C. VIRAL-SPECIFIC LIGANDS OF THE INVENTION

Viral-specific ligands or viral-specific ligands of the invention include extracellular proteins or parts of extracellular proteins as well as any component or part of the extracellular matrix which is able to bind to a virus, thereby guiding the virus to an infection site. The viral-specific ligand can be, without limiatation, a polypeptide, glycopolypeptide, carbohydrate, a protein, a peptide, a lipid, an organic molecule, an inorganic molecule or a combination thereof. Suitable examples of molecules containing viral-specific ligands are shown in Table I. One of skill in the art will recognize that Table I is not an exhaustive list and therefore that the invention is not limited by the table. The molecule DC-SIGN is a dendritic cell (DC)-specific molecule which was recently found to be yet another receptor for HIV. (Geijtenbeek et al., *Cell* 100: 587–597 (2000)). In addition, receptors such as CD21, which binds to the Epstein Barr virus, and the IgA receptor contain viral-specific ligands.

Identification of viral-specific ligands suitable for this invention requires the isolation of a particular virus and the identification of what host component(s) interact with the virus to allow the virus to bind and dock to those cells. One of skill in the art will recognize that the method of the invention is not limited to the disclosed viral-specific ligands but includes any viral-specific ligand to be discovered in the future.

TABLE I

| Virus | Viral-specific ligand |
|---|---|
| Human Rhinovirus (HRV), major group | ICAM-1 |
| Influenza A | sialic acid |
| Adenovirus | vitronectin |
| Epstein-Barr Virus (EBV) | CR2 (C3 receptor) |
| Herpes Simplex Virus type I (HSV I) | heparin sulfate/HveA/HveC |
| Herpes Simplex Virus type II (HSV II) | heparin sulfate/HveA/HveC |
| Poliovirus | Poliovirus Receptor (PVR) |
| Hepatitis B | asialoglycoprotein |
| Human Immunodeficiency Virus (HIV) | CD4, CXCR4, CCR5, DC-SIGN |

Peptide or small molecule libraries (see, e.g., Horwell D. et al. *Immunopharmacology* 33(1–3): 68–72 (1996); Dower W. *Curr Opin Chem Biol* 2(3): 328–34 (1998) for a discussion of the isolation of small molecules that interact with various targets) can also be screened to identify viral-specific ligands. Typically, these libraries of compounds will be small organic, small inorganic molecules and peptides. Essentially any chemical compound can be used as a viral-specific ligand in the invention. Often compounds which can be dissolved in aqueous or organic (especially DMSO-based) solutions are used. Screening assays for viral-specific ligands can be designed to screen large chemical libraries by automating the assay steps and running the assays in parallel (e.g., in microtiter formats on microtiter plates in robotic assays). It will be appreciated that there are many suppliers of chemical compounds, including Sigma (St. Louis, Mo.), Aldrich (St. Louis, Mo.), Sigma-Aldrich (St. Louis, Mo.), Fluka Chemika-Biochemica Analytika (Buchs Switzerland) and the like.

High throughput screening methods for viral-specific ligands can involve providing a combinatorial chemical or peptide library containing a large number of potential viral-specific ligand compounds. A combinatorial chemical library is a collection of diverse chemical compounds generated by either chemical synthesis or biological synthesis, by combining a number of chemical "building blocks" such as reagents. For example, a linear combinatorial chemical library such as a polypeptide library is formed by combining a set of chemical building blocks (amino acids) in every possible way for a given compound length (i.e., the number of amino acids in a polypeptide compound). Millions of chemical compounds can be synthesized through such combinatorial mixing of chemical building blocks.

Preparation and screening of combinatorial chemical libraries is well known to those of skill in the art. Such combinatorial chemical libraries include, but are not limited to, peptide libraries (see, e.g., U.S. Pat. No. 5,010,175, Furka, *Int. J. Pept. Prot. Res.* 37:487–493 (1991) and Houghton et al., *Nature* 354:84–88 (1991)). Other chemistries for generating chemical diversity libraries can also be used. Such chemistries include, but are not limited to: peptoids (e.g., PCT Publication No. WO 91/19735), encoded peptides (e.g., PCT Publication No. WO 93/20242), random bio-oligomers (e.g., PCT Publication No. WO 92/00091), benzodiazepines (e.g., U.S. Pat. No. 5,288,514), diversomers such as hydantoins, benzodiazepines and dipeptides (Hobbs et al., *Proc. Nat. Acad. Sci. USA* 90:6909–6913 (1993)), vinylogous polypeptides (Hagihara et al., *J. Amer. Chem. Soc*. 114:6568 (1992)), nonpeptidal peptidomimetics with glucose scaffolding (Hirschmann et al., *J. Amer. Chem. Soc*. 114:9217–9218 (1992)), analogous organic syntheses of small compound libraries (Chen et al., *J. Amer. Chem. Soc*. 116:2661 (1994)), oligocarbamates (Cho et al., *Science* 261:1303 (1993)), and/or peptidyl phosphonates (Campbell et al., *J. Org. Chem.* 59:658 (1994)), nucleic acid libraries (see Ausubel et al, supra, Berger and Sambrook, all supra), peptide nucleic acid libraries (see, e.g., U.S. Pat. No. 5,539,083), antibody libraries (see, e.g., Vaughn et al., *Nature Biotechnology*, 14(3):309–314 (1996) and PCT/US96/10287), carbohydrate libraries (see, e.g., Liang et al., *Science*, 274:1520–1522 (1996) and U.S. Pat. No. 5,593,853), small organic molecule libraries (see, e.g., benzodiazepines, Baum C&EN, January 18, page 33 (1993); isoprenoids, U.S. Pat. No. 5,569,588; thiazolidinones and metathiazanones, U.S. Pat. No. 5,549,974; pyrrolidines, U.S. Pat. No. 5,525,735 and 5,519,134; morpholino compounds, U.S. Pat. No. 5,506,337; benzodiazepines, 5,288,514, and the like).

Devices for the preparation of combinatorial libraries are commercially available (see, e.g., 357 MPS, 390 MPS, Advanced Chem Tech, Louisville Ky., Symphony, Rainin, Woburn, Me., 433A Applied Biosystems, Foster City, Calif., 9050 Plus, Millipore, Bedford, Me.). In addition, numerous combinatorial libraries are themselves commercially available (see, e.g., ComGenex, Princeton, N.J., Asinex, Moscow, Ru, Tripos, Inc., St. Louis, Mo., ChemStar, Ltd, Moscow, RU, 3D Pharmaceuticals, Exton, Pa., Martek Biosciences, Columbia, Md., etc.).

Such "combinatorial chemical libraries" or "ligand libraries" are then screened in one or more assays to identify those library members (particular chemical species or subclasses) that display a desired viral-specific ligand activity. Assays to identify viral-specific ligand assays can include immunological (e.g., ELISA), radioactive, fluorescent, spectroscopic, etc., methods. Such methods are well known in the art. The compounds thus identified can serve as conventional "lead ligands" or can themselves be used as viral-specific ligands.

Once viral-specific ligands that bind to viral particles or viral molecules are identified, they can be attached to a bacterial-specific ligand (as described below) to produce a chimera that is directed to mucosal bacteria. Viral-specific ligands can also be isolated from phage display libraries (see description below).

D. BACTERIAL-SPECIFIC LIGANDS

Bacterial-specific ligands of the invention include any molecular component, or part thereof, which specifically binds to bacterial flora found on the mucosa. A representative list of bacteria species which inhabit and colonize normal, healthy mucosa is provided in Table II. The listed genera of bacteria or species may be chosen as a target population to which bacteria-specific ligands may bind. This list is not exhaustive and should not be viewed as a limitation to the invention.

TABLE II

Natural Inhabitants of Healthy Mucosal Membranes in Humans

| Nasal/Oral Pharynx | Vaginal | Colon/Rectum |
|---|---|---|
| Streptococcus sps | Lactobacillus sps | Bacteroides sps |
| S. mitis | L. jensensii | Bacillus sps |
| S. oralis | L. crispatus | |
| S. salivalius | L. fermentum | |
| S. pneumoniae | L. casei | |
| Staphylococcus sps | Corynebacterium sps | |
| S. epidermidis | Staphylococcus sps | |
| S. aureus | Streptococcus sps | |
| Neisseria sps | | |
| Lactococcus sps | | |

It is obviously preferred that the bacterial-specific ligand retains its binding property when fused to the viral-specific ligand. Below are four general categories of bacterial-specific ligands followed by specific examples. The bacterial-specific ligands can be, without limitation, any type of molecule, including a peptide, a glycopeptide, a carbohydrate, a lipid.

i. Bacterial cell wall targeting sequences

A number of bacteria secrete proteins which then bind to their own cell surface (e.g., autolysin as described in e.g., Garcia, J. L., et al., 1994, *J. of Bacteriology* 176, 4066–4072 (1994); Wren, B. W., 1991, *Molecular Microbiology* 5, 797–803; and Braun, L. et al., 1997, *Molecular Microbiology*, 25, 285–294) or to a specific target bacteria (e.g. lysostaphin as described in Baba, T. & Schneewind, O., 1996, *Embo Journal* 15, 4789–4797 and Baba, T. & Schneewind, O., 1998, *Embo Journal* 17, 4639–4646.

In general, target specificity is determined by the C-terminal domain of these molecules (known as cell wall targeting sequences as described in Garcia et al., 1994, supra, and Wren, 1991 supra). The best studied of these are molecules which bind specifically to choline, which is a constituent of the cell wall of *Strep. pneumoniae* and a few other bacterial species (*S. oralis*). These molecules include LytA and PspA. Other bacteria-binding molecules include InlB (Braun, et al., supra), which targets *Listeria monocytogenes* and *Bacillus subtilis*, and Lysostaphin (Baba, 1996 supra; Baba, 1998 supra), which targets *Staph. aureus*. The C-terminal (targeting) domains of these molecules to can be used to make chimeric molecules which bind to these particular bacteria.

For example, a domain of ICAM-1 (the receptor for human rhinoviruses, major group) may be genetically fused to the targeting domain of lysostaphin. Chimeric fusion molecules can then be produced which would bind specifically to Staphylococci present on the nasal mucosa. This should significantly enhance the half-life of such chimeric molecules on the nasal mucosa.

Alternatively, the targeting sequences of LytA or PspA may be used to target chimeric ICAM-1 molecules to streptococci and staphylococci.

There are undoubtedly many more such bacterial cell wall targeting sequences in nature. As more proteins which specifically bind to bacterial surface are discovered, the cell wall targeting sequences of these proteins can be determined by making truncations to these molecules and determining the minimal domain which retains cell wall targeting. Such sequences can be used according to the methods of the invention, particularly those that target bacteria present at high levels on a desired mucosa.

ii. Antibody fragments specific for bacterial cell wall fragments

Antibodies, particularly single-chain antibody fragments (scFv) can be rapidly screened for target specificity and then produced in large quantities using a number of expression systems, including bacteria and plants, such as tobacco. Such systems are utilized to screen for scFv specific for common bacterial cell wall structures. Once such antibodies are identified, they can be attached to viral-specific ligands as described below. Although scFv are a preferred embodiment, other antibody fragments such as Fab or Fab' could be used to target the bacteria. Intact antibodies could also be used.

A number of bacterial cell wall components are known and are suitable for use as targets for a chimeric molecule. For instance, peptidoglycan is a common constituent of gram-positive bacterial cell wall (see, e.g., Baron, S., *Medical Microbiology*, 3rd ed., 1991, p. 48), and would serve as a suitable target for scFv molecules of the invention. A number of bacteria, both gram-positive and gram-negative, secrete S-layer proteins which autoaggregate into an S-layer around the bacteria (see, e.g., Singleton, P. and Sainsbury, D., *Dictionary of Microbiology and Molecular Biology*, 2nd ed., 1994, p. 783; *Ann. Rev. Microbiology* 37:311–339 (1983). S-layer proteins, therefore, would be other suitable targets for scFv molecules of the invention.

iii. Peptides or small molecules screened for bacterial specificity

Peptide or small molecule libraries (see, e.g., Horwell D. et al *Immunopharmacology* 33(1–3): 68–72 (1996); Dower W. *Curr Opin Chem Biol* 2(3): 328–34 (1998) for a discussion of the isolation of small molecules that interact with various targets) can also be screened for specificity for bacterial targets as listed in the previous section. Similar to the methods discussed above, combinatorial small molecule and peptide libraries can be screened to identify bacterial-specific ligands. Once small molecules that bind bacteria are identified, they can be attached to a viral-specific ligand (as described below) to produce a chimera that is directed to mucosal bacteria. These small molecules have some advantages over bacterial cell wall targeting sequences and scFv because they would be much smaller, thus reducing the chances of unintended interactions or elicitation of a host immune response.

iv. Carbohydrate bacterial-specific ligands

Carbohydrate can be used as bacterial-specific ligands. For example, it is known that carbohydrate moieties on cells bind to a class of bacterial proteins known as adhesins (For reviews of adhesins, see Soto et al., *J. Bacteriol.*, (1999) 181: 1059–1071; St. Geme, *Advances in Pediatrics*, (1997) 44: 43–72; Ljungh et al., *FEMS Immunol. and Med. Microbiol.*, (1996) 16: 117–126; Ljungh and Wadstreom, *Adv. Exp. Med. and Biol.*, (1996) 408: 129–140. The targets of most bacterial adhesions are carbohydrate moieties on glycoproteins and glycolipids. For example, most *E. coli* express a mannose-specific adhesin, while some also express a galactose-specific adhesin (Wold et al., *Infection and Immunity* (1988) 56 :2531–2537. Thus, mannose and galactose can serve as carbohydrate ligands for some *E. coli*. Also, certain lactobacilli also express a mannose-specific adhesin (Adlerberth et al., *Applied Env. Microbiol.* (1996) 62: 2244–2257).

Suitable examples of bacterial-specific ligands of the invention are shown in Table III. One of skill in the art will recognize that Table II is not an exhaustive list and therefore that the invention is not limited by the table.

TABLE III

| Ligand | Target |
| --- | --- |
| LytA/PspA (C-terminal) | *Streptococcus pneumoniae* (choline) *Streptococcus oralis* |
| InlB (C-terminal) | *Listeria monocytogenes* *Bacillus subtilis* |
| Lysostaphin (SPA$_{CWT}$) | *Staphylococcus aureus* |
| Anti-peptidoglycan Ab fragments | all gram-positive bacteria |
| Ab fragments specific for S-layer proteins | certain lactobacilli and other gram-positive bacteria |

E. CHIMERIC MOLECULES OF THE INVENTION

Chimeric molecules of the invention comprise at least two portions, a viral-specific ligand which is able to bind viral particles, and a bacterial-specific ligand, which target the viral-specific ligand to bacteria on a mucosal membrane. Antibodies can be used as viral-specific ligands in the present invention. Antibodies, particularly single-chain antibody fragments (scFv) can be rapidly screened for target specificity and then produced in large quantities using a number of expression systems, including bacteria and plants, such as tobacco. Such systems are utilized to screen for scFv specific for viral antigens, proteins, lipids and carbohydrates. Once such antibodies are identified, they can be attached to bacterial-specific ligands as described herein. Although scFv are a preferred embodiment, other antibody fragments such as Fab or Fab' could be used to comprise the viral-specific ligands. Intact antibodies could also be used. A number of viral molecules are known and are suitable for use as targets for viral-specific ligands. Methods exist for the cloning of IgG sequences that recognize viral antigens, e.g., measles virus antigens (Burgoon et al., *J Immunol.* 163: 3496–3502 (1999)). Other method for identifying antibodies in a phage display library are detailed below.

i. Genetic methods for producing chimeric molecules

Chimeras of the invention may be obtained by the isolation of nucleic acids encoding respective chimera partners (viral-specific ligands and bacterial-specific ligands), subsequent ligation and production as fusion molecules. Alternatively, partner molecules can be bound together by chemical (covalent) conjugation or via non-covalent linkage.

a. Methods for Isolation and manipulation of recombinant DNA

Methods for the isolation and manipulation of recombinant DNA are routine. Basic texts disclosing the general methods of use in this invention include Sambrook et al., *Molecular Cloning, A Laboratory Manual* (2nd ed. 1989); Kriegler, *Gene Transfer and Expression: A Laboratory Manual* (1990); and *Current Protocols in Molecular Biology* (Ausubel et al., eds., 1994)).

In general, the nucleic acid sequences encoding individual chimera partners or domains are obtained from cDNA and genomic DNA libraries or isolated using amplification techniques with oligonucleotide primers. To make a cDNA library, one should choose a source that is rich in the desired target mRNA. The mRNA is then made into cDNA using reverse transcriptase, ligated into a recombinant vector, and transfected into a recombinant host for propagation, screening and cloning. Methods for making and screening cDNA libraries are well known (see, e.g., Gubler & Hoffman, *Gene* 25:263–269 (1983); Sambrook et al., supra; Ausubel et al., supra).

For a genomic library, the DNA is extracted from the tissue and either mechanically sheared or enzymatically digested to yield fragments of about 12–20 kb. The fragments are then separated by gradient centrifugation from undesired sizes and are constructed in bacteriophage lambda vectors. These vectors and phage are packaged in vitro. Recombinant phage are analyzed by plaque hybridization as described in Benton & Davis, *Science* 196:180–182 (1977).

An alternative method of isolating nucleic acids encoding either part of the viral-specific ligand /bacterial-specific ligand chimera combines the use of synthetic oligonucleotide primers and amplification of an RNA or DNA template (see U.S. Pat. Nos. 4,683,195 and 4,683,202; *PCR Protocols: A Guide to Methods and Applications* (Innis et al., eds, 1990)). Methods such as polymerase chain reaction (PCR) and ligase chain reaction (LCR) can be used to amplify nucleic acid sequences encoding fusion partners directly from mRNA, from cDNA, from genomic libraries or cDNA libraries. Oligonucleotides can be designed to amplify nucleic acids encoding known sequences.

Alternatively, phage display technology can be used to identify peptide viral-specific ligands or bacterial-specific ligands (Smith, G.P. *Science*, 228: 1315–1317(1985)). Briefly, combinatorial peptide sequences or sequences can be cloned into a phage vector that produces a fusion protein with a phage capsid protein that is displayed on the surface of the phage (See Kay et al., eds., *Phage Display ofPeptides and Proteins* (1996) for review of phage display methods). The foreign protein fused with the capsid protein is accessible to binding substrates and thus permits a library of phage to be screened for their ability to bind to a ligand of interest. In the present invention, the phage display library can encode antibody fragments (e.g., Fab), single chain antibodies, combinatorial peptides, naturally occurring sequences, or combinations thereof.

Phage display technology has been used to identify viral-specific ligands. For example, high-affinity human anti-viral antibodies have been identified using phage display technology for HIV-1, RSV (respiratory syncytial virus) and herpes simplex viruses 1 and 2 (See review, Barbas and Burton, *Trends Biotechnol*., 14: 230–234 (1996). The sequences that form the phage display library can be comprised of sequences from a subject sero-positive for the virus of interest (Björling et al., *J. Gen. Virol*. 80: 1987–1993 (1999)). For example, human Fab fragments reacting with HIV-1 surface glycoprotein gp120 can be identified from a phage display library of IgG1κ sequences from a long term asymptomatic HIV-seropositive patient (Barbas et al., *J. Mol Biol*. 230: 812–823 (1993)). Randomized or partially randomized peptide libraries can also be screened to identify Fab peptides that bind to the HIV-1 envelope glycoprotein gp120 using phage display (Ferrer and Harrison, *J. Virol*. 73: 5795–5802 (1999). The nucleic acid sequences from the identified phage can be cloned and used as a viral-specific ligand.

Once the nucleic acid sequences encoding the two components of the chimera are isolated, they are readily fused to form a contiguous nucleic acid encoding the chimeric protein. Typically, the two components are amplified using amplification primers that incorporate a restriction enzyme site that affords the ability to cleave and ligate in the desired orientation (see, e.g., Ausubel et al., *Current Protocols in Molecular Biology*, Volumes 1–3, John Wiley & Sons, Inc. (1994–1998)).

In a preferred embodiment, the viral-specific ligand/bacterial-specific ligand chimeras of the invention are synthesized using recombinant nucleic acid techniques. After the gene encoding a viral-specific ligand/bacterial-specific ligand chimera is created, it is ligated into an expression cassette under the control of a particular promoter, expressing the protein in a host, isolating the expressed protein and, if required, renaturing the protein. Techniques sufficient to guide one of skill through such procedures are found in, e.g., Sambrook et al., *Molecular Cloning—A Laboratory Manual*, Cold Spring Harbor Laboratory, Cold Spring Harbor, New York, (1989) or Ausubel et al.

Finally, synthetic oligonucleotides can be used to construct recombinant genes for expression of protein of the chimeras of this invention. Oligonucleotides can be chemically synthesized according to the solid phase phosphoramidite triester method first described by Beaucage & Caruthers, *Tetrahedron Letts*. 22:1859–1862 (1981), using an automated synthesizer, as described in Van Devanter et. al., *Nucleic Acids Res*. 12:6159–6168 (1984). Purification of oligonucleotides is by either native acrylamide gel electrophoresis or by anion-exchange HPLC as described in Pearson & Reanier, *J. Chrom*. 255:137–149 (1983).

In particular, this method is performed using a series of overlapping oligonucleotides usually 40–120 bp in length, representing both the sense and nonsense strands of the gene. These DNA fragments are then annealed, ligated and cloned. Alternatively, amplification techniques can be used with precise primers to amplify a specific subsequence of the gene of interest. The specific subsequence is then ligated into an expression vector.

The sequence of the cloned genes and synthetic oligonucleotides can be verified after cloning using, e.g., the chain termination method for sequencing double-stranded templates of Wallace et aL, *Gene* 16:21–26 (1981).

b. Methods for expression of recombinant nucleic acids

Once the desired gene is cloned, it is expressed to obtain the chimeric protein or its components. To obtain high level expression of a cloned gene, one typically subclones the gene of interest (e.g., a chimera partner) into an expression vector that contains a strong promoter to direct transcription, a transcription/translation terminator, and if for a nucleic acid encoding a protein, a ribosome binding site for translational initiation. Suitable bacterial promoters are well known in the art and described, e.g., in Sambrook et al. and Ausubel et al. Bacterial expression systems for expressing the protein are available in, e.g., *E. coli*, Bacillus sp., and Salmonella (Palva et al., *Gene* 22:229–235 (1983); Mosbach et al., *Nature* 302:543–545 (1983). Kits for such expression systems are commercially available. Eukaryotic expression systems for mammalian cells, yeast, and insect cells are well known in the art and are also commercially available.

Selection of the promoter used to direct expression of a heterologous nucleic acid depends on the particular application. The promoter is preferably positioned about the same distance from the heterologous transcription start site, as it is from the transcription start site in its natural setting. As is known in the art, however, some variation in this distance can be accommodated without loss of promoter function.

In addition to the promoter, the expression vector typically contains a transcription unit or expression cassette that contains all the additional elements required for the expression of the chimera partner-encoding nucleic acid in host cells. A typical expression cassette thus contains a promoter operably linked to the nucleic acid sequence encoding a chimera partner or the chimeric molecule and signals required for efficient polyadenylation of the transcript, ribosome binding sites, and translation termination. A cleavable signal peptide sequence to promote secretion of the encoded protein by the transformed cell may be included in the construct. Additional elements of the cassette may include enhancers and, if genomic DNA is used as the structural gene, introns with functional splice donor and acceptor sites.

The elements that are typically included in expression vectors also include a replicon that functions in *E. coli*, a gene encoding antibiotic resistance to permit selection of bacteria that harbor recombinant plasmids, and unique restriction sites in nonessential regions of the plasmid to allow insertion of eukaryotic sequences. The particular antibiotic resistance gene chosen is not critical; any of the many resistance genes known in the art arc suitable. The prokaryotic sequences are preferably chosen such that they do not interfere with the replication of the DNA in eukaryotic cells, if necessary.

Any of the well-known procedures for introducing foreign nucleotide sequences into host cells may be used. These include the use of calcium phosphate transfection, polybrene, protoplast fusion, electroporation, liposomes, microinjection, plasma vectors, viral vectors and any of the other well known methods for introducing cloned genomic DNA, cDNA, synthetic DNA or other foreign genetic material into a host cell (see, e.g., Sambrook et al., supra).

After the expression vector is introduced into the cells, the transfected cells are cultured under conditions favoring expression of the fusion or fusion partner, which is recovered from the culture using standard techniques identified below.

c. Methods for purification of polypeptides of the invention

The chimera partners or the chimeric molecules may be purified to substantial purity by standard techniques, including selective precipitation with such substances as ammonium sulfate; column chromatography, immunopurification methods, and others (see, e.g., Scopes, *Protein Purification: Principles and Practice* (1982); U.S. Pat. No. 4,673,641; Ausubel et al., supra; and Sambrook et al., supra).

A number of procedures can be employed when recombinant fusions or fusion partners are purified. For example, proteins having established molecular adhesion properties can be reversibly fused to the chimera partners or the chimeric molecule. With the appropriate ligand, the chimera partners or the chimeric molecules can be selectively adsorbed to a purification column and then freed from the column in a relatively pure form. The ligand is then removed by enzymatic activity. Finally the chimera partners or the chimeric molecules could be purified using immunoaffinity columns.

ii. Non-genetic methods for producing a chimeric molecule

Chimeric molecules of the invention can be formed in a variety of ways. Chimeras are generally formed by combining a viral-specific ligand with a bacterial-specific ligand. The soluble viral-specific ligand and the bacterial-specific ligand can be bound together via covalent bonds or through ionic interactions and hydrogen bonding. In addition, it will be readily apparent to those of skill in the art that the viral-specific ligand and bacterial ligand molecules can also comprise additional molecules, e.g., an antibody, or can be contained in another molecule, e.g., a liposome, to help direct the viral-specific ligand or the chimera partners to the target site of interest.

a. Chemical conjugation of the viral-specific ligand to the bacterial binding protein In one embodiment of the invention, the soluble viral-specific ligand is chemically conjugated to a bacterial-specific ligand via covalent bonding. Means of chemically conjugating molecules are well known to those of skill. See, for instance, U.S. Pat. No. 5,856,125 for a discussion of means of conjugating molecules. The procedure for attaching the viral-specific ligand to a bacterial-specific ligand varies according to the chemical structure of the bacterial ligand. Polypeptides typically contain a variety of functional groups; e.g., carboxylic acid (COOH) or free amine (—$NH_2$) groups, which are available for reaction with a suitable functional group on either the viral-specific ligand or bacterial targeting protein. Alternatively, polypeptides are derivatized to attach additional reactive functional groups.

A "linker", as used herein, is a molecule that is used to join the soluble viral-specific ligand to a bacterial mucosal surface protein. The linker is capable of forming covalent bonds to both the viral-specific ligand and the bacterial-specific ligand. Suitable linkers are well known to those of skill in the art and include, but are not limited to, straight or branched-chain carbon linkers, heterocyclic carbon linkers, or peptide linkers. When the viral-specific ligand and the bacterial-specific ligand are both polypeptides, the linkers can be joined to the constituent amino acids through their side groups (e.g., through a disulfide linkage to cysteine), or to the alpha-carbon amino and carboxyl groups of the terminal amino acids.

In addition, a bifunctional linker having one functional group reactive with a group on a particular ligand, and another group reactive with a nucleic acid binding molecule, can be used to form the desired conjugate. Alternatively, derivatization can proceed through chemical treatment of the bacterial targeting protein or the viral-specific ligand. For instance, chemical treatment of a glycoprotein involves glycol cleavage of the sugar moiety of a glycoprotein with periodate to generate free aldehyde groups. The free aldehyde groups on the glycoprotein may be reacted with free amine or hydrazine groups on an agent to bind the agent thereto (see, e.g., U.S. Pat. No. 4,671,958). In another example, free sulfhydryl groups can be generated on polypeptides (see, e.g., U.S. Pat. No. 4,659,839).

Heterobifunctional linkers, such as maleimide-hydroxysuccinimide ester, can also be used as selective linkages (see, e.g., U.S. Pat. No. 5,851,527). Reaction of maleimide-hydroxysuccinimide ester with a viral-specific ligand protein will derivatize amine groups on the protein, and the derivative can then be reacted with, e.g., a bacterial ligand protein with free sulfhydryl groups. Many other procedures and linker molecules for attachment of various compounds to proteins are known. See, for example, European Patent Application No. 188,256; U.S. Pat. Nos. 4,671, 958; 4,659,839; 4,414,148; 4,699,784; 4,680,338; 4,569, 789; 5,856,571; 5,824,805; 5,470,997; 5,470,843; 5,470, 932; 5,843,937 and 4,589,071; and Borlinghaus et al. *Cancer Res.* 47:4071–4075 (1987).

b. Preparation of fusion proteins

When both the viral-specific ligand and the bacterial-specific ligand are relatively short proteins, a chimeric molecule is optionally synthesized as a single contiguous polypeptide using standard chemical peptide synthesis techniques. Alternatively, the viral-specific ligand and the bacterial-specific ligand can be synthesized separately, and then fused by condensation of the amino terminus of one molecule with the carboxyl terminus of the other molecule, thereby forming a peptide bond. In another alternative, the viral-specific ligand and the bacterial-specific ligand can each be condensed with one end of a peptide spacer molecule thereby forming a contiguous fusion protein.

Alternatively, fusion proteins can be produced by solid phase synthesis in which the C-terminal amino acid of the sequence is attached to an insoluble support followed by sequential addition of the remaining amino acids in the sequence. Techniques for solid phase synthesis are described by Barany and Merrifield, *Solid-Phase Peptide Synthesis*; pp. 3–284 in *The Peptides: Analysis, Synthesis, Biology*. Vol. 2: Special Methods in Peptide Synthesis, Part A.; Merrifield, et al., *J. Am. Chem. Soc.*, 85:2149–2156 (1963), and Stewart et al., *Solid Phase Peptide Synthesis*, 2nd ed. Pierce Chem. Co., Rockford, Ill. (1984) which are incorporated herein by reference.

While a viral-specific ligand and a bacterial-specific ligand are often joined directly together, one of skill will appreciate that the molecules may be separated by a peptide spacer consisting of one or more amino acids. Generally, the spacer will have no specific biological activity other than to join the proteins or to preserve some minimum distance or other spatial relationship between them. However, the constituent amino acids of the spacer may be selected to influence some property of the molecule such as the folding, net charge, or hydrophobicity.

Once expressed, the recombinant chimeric fusion proteins can be purified according to standard procedures, including ammonium sulfate precipitation, affinity columns, column chromatography, gel electrophoresis and the like (see, generally, R. Scopes, Protein Purification, Springer-Verlag, N.Y. (1982), Deutscher, Methods in Enzymology Vol. 182: Guide to Protein Purification., Academic Press, Inc. N.Y. (1990)). Substantially pure compositions of about 50 to 95% homogeneity are preferred, and 80 to 95% or greater homogeneity are most preferred for use in the methods of the invention.

One of skill in the art will recognize that after chemical synthesis, biological expression and/or purification, the fusion molecules of the invention may possess a conformation substantially different than the native conformations of the constituent polypeptides. In this case, it is often necessary to denature and reduce the polypeptide and then to cause the polypeptide to re-fold into the preferred conformation. Methods of reducing and denaturing proteins and inducing re-folding are well known to those of skill in the art (see, e.g., Debinski, et al., *J. Biol. Chem.*, 268:14065–14070

(1993); Kreitman and Pastan, *Bioconjug. Chem.*, 4:581–585 (1993); and Buchner, et al., *Anal. Biochem.*, 205:263–270 (1992)). Finally, non-functional chimeras can be separated from functional chimeras by standard chromatographic techniques which releasably and selectively bind the functional chimeras and allow nonfunctional chimeras to pass.

c. Immuno-targeting of viral-specific ligands to the bacterial binding protein

The viral-specific ligand can also be targeted to the bacterial mucosal surface by immuno-targeting. It is well known that antibodies or antibody fragments can be conjugated to various molecules (e.g., polypeptides, radioisotopes, drugs, toxins, etc.) to target the molecules to a particular site (see, e.g., U.S. Pat. Nos. 4,046,722; 4,699,784; 4,332,647; 4,348,376; 4,361,544; 4,468,457; 4,444,744; 4,460,459; 4,624,846; 5,698,178; 5,057,313 and 4,460,561.). Such antibodies can be used to target the viral-specific ligand to bacterial targets directly or can act as linkers to bind to bacterial-specific ligands that subsequently target the viral-specific ligand to bacteria on the mucosa.

It is advantageous to covalently bind the viral-specific ligand to the antibody (see, e.g., U.S. Pat. No. 5,851,527). The binding can be direct or through a short or long linker moiety and acts through one or more functional groups on the antibody and/or the enzyme, e.g., amine, carboxyl, phenyl, thiol or hydroxyl groups. Various conventional linkers can be used, e.g., disiocyanates, diisothiocyanates, bis(hydroxysuccinimide) esters, carbodiimides, maleimide-hydroxysuccinimide esters, glutaraldehyde and the like, as well as any other linker described above.

If the viral-specific ligand is a protein, a simple method to bind an antibody to the viral-specific ligand is to mix the antibody with the viral-specific ligand protein in the presence of glutaraldehyde to form an antibody-protein conjugate. The initial Schiff base linkages can be stabilized, e.g., by borohydride reduction to secondary amines. A diisothiocyanate or a carbodiimide can be used in place of glutaraldehyde.

More selective linkage can be achieved by using a heterobifunctional linker such as a maleimide-hydroxysuccinimide ester. Reaction of the latter with an enzyme will derivatize amine groups on the viral-specific ligand protein, and the derivative can then be reacted with, e.g., an antibody Fab fragment with free sulfhydryl groups (or a larger fragment or intact immunoglobulin with sulfhydryl groups appended thereto by, e.g., Traut's Reagent).

It is advantageous to link the viral-specific ligand to a site on the antibody remote from the antigen binding site. This can be accomplished by, e.g., linkage to cleaved interchain sulfhydryl groups, as noted above. Another method involves reacting an antibody whose carbohydrate portion has been oxidized, with a viral-specific ligand protein that has at least one free amine function. This results in an initial Schiff base (imine) linkage, which is preferably stabilized by reduction to a secondary amine, e.g., by borohydride reduction, to form the final conjugate.

Because of the size of the conjugate, it will preferably comprise one antibody linked to one viral-specific ligand molecule. It may be advantageous, however, to bind a plurality of antibody fragments, e.g., Fab or $F(ab')_2$ fragments, to a single viral-specific ligand to increase its binding affinity or efficiency to the antigen target. Alternatively, if the viral-specific ligand is not too bulky, it may be useful to link a plurality of viral-specific ligand molecules to a single antibody or antibody fragment. Conjugates of more than one viral-specific ligand and antibody can also be used, provided they can reach the target site and they do not clear from the mucosa too fast. Mixtures of different sized conjugates, or conjugates that contain aggregates can be used, again with the same caveats just noted.

F. DETERMINATION OF CHIMERIC MOLECULE BINDING TO MUCOSAL BACTERIA AND VIRUS IMMOBILIZATION

Once a chimeric molecule has been prepared, it is necessary to determine the efficiency with which the chimera can bind mucosal bacteria. The method below describes several alternative methods for testing chimeric molecule binding.

Chimeric molecules are mixed with the target bacteria and allowed to bind onto the bacterial surface. After a washing step, chimeric molecules bound on the bacterial surface can be detected in at least two convenient ways. Antibodies specific for the viral-specific ligand can be added and allowed to bind to the chimeric molecules. By using secondary antibodies that are directly conjugated to a fluorescent dye (e.g. FITC or PE), antibodies bound to bacteria can be visualized using FACS analysis or fluorescence microscopy. For example, chimeric molecules which target CD4 (the receptor for HIV) to lactobacilli are mixed with the appropriate bacteria. These bacteria are washed, incubated with FITC-labeled anti-CD4 antibodies, washed again, then analyzed by flow cytometry. Fluorescence of bacteria in the FITC channel (FL1) indicates the relative amount of FITC-conjugated antibodies bound per bacterium, which is directly proportional to the number of bound chimeric molecules. Alternatively, bacteria may be viewed using a microscope under UV light. Fluorescence around each bacteria indicates binding of chimeric molecules onto the bacterial surface.

To test for the ability of the bacteria chimera protein complex to bind or immobilize virus, the intact virus or the viral-specific ligand itself can be used to measure receptor binding. For instance, in the CD4 example above, gp120, the CD4 ligand, is labeled with an appropriate dye, and the relative binding of gp120 to bacteria with or without the chimeric molecule is determined. As another alternative, the dye could instead be attached to an anti-gp120 antibody that can then be used to determine relative binding.

Suitable binding exists where the binding of bacteria to chimera is sufficiently selective such that the binding is at least two times greater than the viral-specific ligand not modified to bind to the bacterial surface. Viral binding is suitable when viral binding is at least twice background using unmodified bacteria as a control. Both tests presume adequate scientific method and principles are being used to control for random error.

G. PHARMACEUTICAL FORMULATIONS OF THE INVENTION

The chimeric molecules of the invention are suitable for preparation as pharmacological formulations. The chimeras may be mixed with pharmaceutically-acceptable excipients which are compatible with the peptides and are pharmaceutically acceptable. Suitable excipients may include water, saline, dextrose, glycerol, ethanol, and combinations thereof. The chimeric molecules may further contain auxiliary substances such as wetting or emulsifying agents or pH buffering agents to enhance the uptake of the chimeras.

More specifically, the chimeric molecules of this invention may be combined or mixed with various solutions and other compounds as is known in the art. For example, it may be administered in unit doses in water, saline or buffered vehicles.

Conveniently, the formulations of the invention are prepared to contain a final concentration of chimeric molecule in the range of from 0.2 to 200 µg/ml, preferably 5 to 50 µg/ml, and more preferably 10–30 µg/ml. After formulation, the chimeric molecules may be incorporated into a sterile container that is then sealed and stored at a low temperature, for example 4° C., or it may be freeze-dried and resuspended in a suitable buffer prior to use. Lyophilization permits long-term storage of the chimeric molecules in a stabilized form.

Suitable formulations for vaginal administration include, for example, creams, gels, suppositories, or tampons. For instance, U.S. Pat. No. 5,840,685 teaches pharmaceutical compositions for intervaginal administration including an absorption promoter such as an anionic or nonionic surfactant and an aliphatic carboxylic acid. Optionally animal or vegetable protein, such as bovine serum albumin can be added to the composition to promote stability of the active ingredient. Discussion of other methods of vaginal formulations can be found in U.S. Pat. Nos. 4,659,969, 4,670,419, 4,609,640 and 3,917,825.

Suppositories, binders and carriers may include, for example, polyalkalene glycols or triglycerides. Oral formulations may include normally employed incipients such as, for example, pharmaceutical grades of saccharine, cellulose and magnesium carbonate. These compositions take the form of solutions, suspensions, tablets, pills, capsules, sustained release formulations or powders and contain 10–95% of the chimeras.

The chimeric molecules of this invention can be formulated for administration via the nasal passages. Formulations suitable for nasal administration, wherein the carrier is a solid, include a coarse powder having a particle size, for example, in the range of about 10 to about 500 microns. Suitable formulations wherein the carrier is a liquid can also be provided.

H. ADMINISTRATION

One of skill in the art will recognize that application of formulations of this invention to mucosal membranes can be performed in a number of ways. It is preferred, however, that pharmacological formulations of this invention be applied to mucosal membranes so that the viral-specific ligands of the invention can interact with their targets on the various mucosal membranes of the body. For instance, the formulations can be administered nasally, orally, by suppository or by vaginal douching.

Pharmacological application of chimeric molecules of this invention can be performed by way of nasal administration, among other methods. Various methods of nasal administration are known in the art. The pharmaceutical formulation for nasal administration may be prepared as solutions in saline, employing benzyl alcohol or other suitable preservatives, absorption promoters to enhance bioavailability, fluorocarbons, and/or other solubilizing or dispersing agents known in the art. Suitable liquid formulations can be administered, for example, as nasal spray, nasal drops, or by aerosol administration by nebulizer, include aqueous or oily solutions of the active ingredient.

Devices for delivering nasal sprays are known. These are typically hand-held containers (5) designed to hold fluids (FIG. 2). The preferred container comprises two ends with one end being a flexible base (6) and the second end being a tip (7) having a blunt taper ending in an opening in communication with the fluid in the base (FIG. 2). The blunt taper allows for partial insertion of the tip and opening into a nostril. When the flexible base is squeezed, a metered volume of aerosol fluid is delivered through an opening in the tip (8) into the nose for inhalation and delivery to the nasal mucosal membranes (FIG. 2).

Powder formulations suitable for nasal administration are administered in the manner in which snuff is taken, i.e., by rapid inhalation through the nasal passage from a container of the powder held close up to the nose. For further discussions of nasal administration of polypeptides, references are made to the following patents, U.S. Pat. Nos. 5,877,163, 5,846,978, 5,747,445, 5,663,169, 5,578,597, 5,502,060, 5,476,874, 5,413,999, 5,308,854, 5,192,668, and 5,187,074.

Formulations suitable for vaginal administration may be presented as pessaries, tampons, creams, gels, pastes, foams or spray formulations containing in addition to the active ingredient such carriers as are known in the art to be appropriate.

Rectal administrations are typically done with suppositories. Various compositions used in such suppositories include those discussed in U.S. Pat. Nos. 5,859,048 and 5,759,566.

Oral administration can be performed preferably through the form of a mouthwash.

The efficacy of the administration will depend on a number of criteria, including the time of contact of the active ingredient with the mucosal membrane.

The following Examples are offered by way of illustration, not limitation. Those of skill will readily recognize a variety of non-critical parameters which could be changed or modified to yield essentially similar results. All references cited in this specification are incorporated herein by reference.

EXAMPLES

Example 1

ICAM—$SPA_{CWT}$ (Genetic Fusion)

The polypeptide comprising ICAM-1 domains 1 and 2 (the minimal receptor for human rhinovirus, HRV, major group (see, e.g., Casasnovas, J. M. and Springer, T. A., *Journal of Virology* 68, 5882–5889 (1994); Casasnovas, J. M., et al., *Journal of Virology* 72, 6244–6246 (1998)) is expressed as a fusion protein with the C-terminal domain of lysostaphin, $SPA_{CWT}$ (see, e.g., Baba, T. and Schneewind, O., *EMBO J.* 15, 4789–4797 (1996) and Baba, T. and Schneewind, O., *EMBO J.* 17, 4639–4646 (1998)), to target this chimeric molecule to the surface of *Staphlyococcus aureus*. The DNA fragments coding for domains 1 and 2 of ICAM-1 and $SPA_{CWT}$ are amplified using polymerase chain reaction (PCR) with primers designed to introduce in-frame EcoRI restriction sites flanking residues 1–168 of ICAM-1 and residues 389–480 of lysostaphin ($SPA_{CWT}$). These fragments are ligated together and placed into a mammalian expression cassette for expression in mammalian cell lines, and contains the selectable marker Herpes thymidine kinase (TK).

Chimeric molecules are expressed in Chinese Hamster Ovarian (CHO) cells. The expression vector containing the DNA fragments coding for ICAM-1 domains 1 and 2 and $SPA_{CWT}$ is transfected into CHO cells under standard conditions. These cells are grown up in large numbers in standard culture medium (Dulbecco's modified essential medium containing 10% fetal bovine serum); transfectants are selected by the addition of HAT (hypoxanthine/aminopotherin/thymidine) to the medium to maintain selective pressure for the marker Herpes TK. After a growth period of 48–96 hours, cells are lysed to release the cytosolic contents containing the chimeric molecules. Cells are solubilized for 1 hour at 4° C. in a physiologic buffer (phosphatebuffered saline) containing the non-ionic detergent Triton X-100 and a cocktail of protease inhibitors (aprotinin and leupeptin at 10 μg/ml, EDTA at 1 mM) to prevent proteolytic degradation of the chimeric molecules.

Chimeric molecules are purified using monoclonal antibody affinity chromatography. The monoclonal antibody RR1/1, which reacts with ICAM-1, is coupled to an inert column matrix. The cell lysate from CHO cells containing chimeric molecules is passed through precolumns to remove materials that bind non-specifically to the column matrix material, then through the RR1/1-immobilized column. The ICAM-1 moiety of the chimeric molecule will bind the antibody and be immobilized on the column. The column is then washed extensively with a series of detergent wash buffers of increasing pH, up to pH 11.0. During these washes, chimeric molecules remain bound to the column, while non-binding and weakly binding contaminants are removed. The bound chimeric molecules are then specifically eluted from the column by applying a detergent buffer of pH 12.5.

Example 2

Sialic acid—scFv Specific for Peptidoglycan (Chemical Linkage)

Sialic acids (Fluka Chemicals LTD, Switzerland) are chemically linked to single-chain variable antibody fragments (scFv) specific for peptidoglycan (the major constituent of the cell wall of all gram-positive bacteria). This conjugation is carried out using one of several heterobifunctional crosslinkers, such as ABH or MPBH (Pierce Inc. USA).

ABH consists of a hydrazide group that reacts with the cis-diol moiety in sialic acid, and a photoazide end that reacts non-specifically with scFv upon UV photolysis. Like ABH, MBPH contains a hydrazide group that reacts with the cis-diol moiety in sialic acid. However, instead of a non-specific photoazide group, MBPH contains a maleimide group that reacts specifically with the—SH group in scFv, forming a thioether linkage upon coupling.

After conjugation, sialic acid-linked scFv products are extensively purified away from unconjugated material using affinity chromatography. The reaction mixtures are first fractionated using an S-200 column in FPLC, which separates molecules based on size. Material from the peak of appropriate size is further purified using anion exchange (MonoQ) chromatography.

One skilled in the art can determine when they have a functional conjugate, i.e. it binds bacterial surface via peptidoglycan and influenza A virus via sialic acid, in several ways. For example, conjugates may be added together with gram-positive bacteria and fluorescent-labeled influenza A viral particles. If functional conjugates exist, they should bind gram-positive bacteria on one end, and viral particles on the other, forming a bridge. Viral particles associated with bacterial surface may be detected by inspection under fluorescent microscopy.

Example 3

CD4—scFv Specific for S-Proteins (Biotin-Avidin Linkage)

A number of gram-positive and gram-negative bacteria synthesize S-layer proteins, which autoaggregate into an S-layer surrounding the bacterial surface. A number of lactobacillus strains on the vaginal flora produce S-layer proteins. ScFv specific for S-layer proteins are linked to CD4, the receptor for HIV, using biotin-avidin crosslinking. A 15-amino acid peptide (BSP for biotin substrate peptide), the substrate for the enzyme BirA, is genetically fused to the COOH-terminus of the scFv and domains 1 and 2 of CD4 using the method described by Altman et al. (*Science* 274, 94–96 (1996)). Briefly, DNA coding for a GlySer linker and BSP are fused to the 3' end of the DNA fragments coding for the scFv and domains 1 and 2 of CD4. BSP-containing proteins are expressed in CHO cells as in example 1 and then biotinylated specifically on the lysine residue of BSP using the enzyme BirA. Alternatively, unmodified CD4 (domains 1 and 2) and scFv are expressed in CHO cells and purified as in example 1. These molecules are biotinylated on amine groups using NHS-esters of biotin (Pierce Inc. USA).

Biotinylated CD4 and scFv are mixed together at equal molar ratios. Avidin is then added at one-fourth molar ratio (each avidin has four binding sites for biotin) to bring biotinylated CD4 and scFv together into multimeric complexes. At this point, complexes consist of CD4:scFv at the ratios of 0:4, 1:3, 2:2, 3:1, and 4:0. These different complexes are separated using affinity chromatography. Each complex eludes from an S-200 column in FPLC at a distant fraction. The fractions corresponding to complexes of CD4:scFv at the ratios of 1:3, 2:2, and 3:1 are collected and pooled. These complexes are then further purified using anion exchange (MonoQ) chromatography.

Example 4

The Use of ICAM-1/$SPA_{CWT}$ in Nasal Spray to Prevent Rhinovirus Infections

Chimeric ICAM-1/$SPA_{CWT}$ molecules, produced in CHO cells and purified by affinity chromatography, are stored in sterile saline at 30 $\mu$g/ml. A nasal spray containing this solution may be used by persons at risk for human rhinovirus exposure, such as health care workers or flight attendants. Such persons may administer one spray to each nostril daily during periods of maximal contact, e.g. during the winter season. Other circumstances when such a product may be useful include prior to exposure to an infected individual, or one week before an important meeting or event when a person cannot afford to become ill.

What is claimed is:

1. A method of increasing the half life of a viral-specific ligand to be administered on a mucosal membrane of an animal wherein said membrane is colonized with bacteria, said method comprising: contacting the mucosal membrane with a chimeric molecule comprising said viral-specific ligand and a bacterial-specific ligand which is specific for bacteria colonizing the membrane.

2. The method of claim 1, wherein said bacteria colonizing the mucosal membrane are selected from the genera consisting of Lactobacillus, Streptococcus, Staphylococcus, Lactococcus, Bacteriodes, Bacillus, and Neisseria.

3. The method of claim 1, wherein said bacterial-specific ligand is an antibody.

4. The method of claim 3, wherein said antibody is an antibody selected from the group consisting of: a single chain antibody, a F(ab), and a F(ab)2.

5. The method of claim 1, wherein said bacterial-specific ligand is comprised of a peptide, a polypeptide, a protein, a carbohydrate, or a combination thereof.

6. The method of claim 1, wherein said bacterial-specific ligand is selected from the group consisting of:

a C-terminal choline binding domain of LytA, a C-terminal choline binding domain of PspA, a C-terminal domain of lysostaphin (SPACWT), a C-terminal domain of InlB, an anti-S-layer protein antibody, and an anti-peptidoglycan antibody.

7. The method of claim 1, wherein said viral-specific ligand is modified by binding a bacterial-specific ligand to said viral-specific ligand via a bifunctional linking reagent.

8. The method of claim 1, wherein said viral-specific ligand is modified by covalently binding a bacterial-specific ligand to said viral-specific ligand.

9. The method of claim 1, wherein said viral-specific ligand and the bacterial-specific ligand are joined through a peptide linker.

10. The method of claim 1, wherein said viral-specific ligand is an antibody.

11. The method of claim 10, wherein said antibody is selected from the group consisting of: a single-chain antibody, a F(ab), and a F(ab)2.

12. The method of claim 1, wherein said viral-specific ligand is comprised of a peptide, a polypeptide, a protein, a carbohydrate, or a combination thereof.

13. The method of claim 1, wherein said viral-specific ligand is comprised of CD4, DC-SIGN, ICAM-1, HveA, HveC, poliovirus receptor, vitronectin receptor, CD21, or IgA receptor sequences.

14. The method of claim 1, wherein said viral-specific ligand is a carbohydrate.

15. The method of claim 14, wherein said carbohydrate is selected from the group comprising sialic acid and heparin sulfate.

16. A method of binding viral particles to bacteria inhabiting the mucosal membrane of an animal comprising the steps of: (i) contacting the bacteria with a chimeric molecule comprising a viral-specific ligand and a bacterial-specific ligand; and, (ii) permitting viral particles specifically recognized by said viral-specific ligand to bind to said bacteria.

17. A pharmaceutical composition comprising a therapeutically effective amount of a chimeric molecule comprising a viral-specific ligand and a bacterial-specific ligand.

18. The pharmaceutical composition of claim 17, wherein said pharmaceutical composition is formulated as a member selected from the group consisting of: a solution, a powder, a cream, a gel, an ointment, a douche, a suspension, a tablet, a pill, a capsule, a nasal spray, a nasal drop, a suppository and an aerosol.

19. The pharmaceutical composition of claim 17, wherein said pharmaceutical composition is formulated as a member selected from the group consisting of: a pessary, a tampon, a gel, a paste, a foam, and a spray.

* * * * *